United States Patent
Kilbey

(10) Patent No.: US 9,498,369 B2
(45) Date of Patent: Nov. 22, 2016

(54) MODULAR SHOULDER EXTERNAL ROTATION WEDGE SYSTEM AND METHOD

(71) Applicant: Bryan E. Kilbey, DeFuniak Sprs, FL (US)

(72) Inventor: Bryan E. Kilbey, DeFuniak Sprs, FL (US)

(*) Notice: Subject to any disclaimer, the term of this patent is extended or adjusted under 35 U.S.C. 154(b) by 630 days.

(21) Appl. No.: 13/886,356

(22) Filed: May 3, 2013

(65) Prior Publication Data

US 2014/0330182 A1    Nov. 6, 2014

(51) Int. Cl.
*A61F 5/37* (2006.01)

(52) U.S. Cl.
CPC ............ *A61F 5/3753* (2013.01); *A61F 5/3738* (2013.01)

(58) Field of Classification Search
CPC .......... A61F 5/00; A61F 5/37; A61F 5/3115; A61F 5/3723; A61F 5/373; A61F 5/3738; A61F 5/3753; A61F 5/3761; A61F 5/40; A61G 13/00; A61G 13/10; A61G 13/12; A61G 13/1205; A61G 13/1235; A61G 13/1255; A61G 13/128; A61G 13/1285; A61G 13/129; A61G 13/1295
USPC ........... 5/630, 636, 640, 646–648, 907, 922, 5/933; 128/845, 846, 869, 876–878; 224/157, 158; 602/3–5, 13, 16, 19–20
See application file for complete search history.

(56) References Cited

U.S. PATENT DOCUMENTS

| | | | | |
|---|---|---|---|---|
| 4,598,701 A * | 7/1986 | Schaefer | ............... | A61F 5/3753 602/19 |
| 4,896,660 A * | 1/1990 | Scott | ..................... | A61F 5/3753 602/20 |
| 5,334,132 A * | 8/1994 | Burkhead | ............. | A61F 5/3738 602/4 |
| 7,189,213 B1 * | 3/2007 | Weber | ....................... | A61F 5/37 602/20 |
| 7,244,239 B2 * | 7/2007 | Howard | ................ | A61F 5/3753 128/878 |
| 7,563,236 B2 * | 7/2009 | Kazmierczak | ........ | A61F 5/3753 602/4 |
| 8,016,780 B1 * | 9/2011 | Sickles | .................. | A61F 5/3715 602/20 |
| 8,109,273 B2 * | 2/2012 | Golden | ............... | A61F 5/05841 128/846 |
| 8,273,040 B1 * | 9/2012 | Morrow | ................ | A61F 5/3738 602/4 |
| 8,273,041 B2 * | 9/2012 | Goumas | ................ | A61F 5/3738 128/845 |
| 8,414,512 B2 * | 4/2013 | Fout | ...................... | A61F 5/3753 128/869 |
| 8,523,795 B2 * | 9/2013 | McCune | ............... | A61F 5/3753 602/4 |
| 2003/0187373 A1 * | 10/2003 | Gaylord | ................ | A61F 5/3753 602/4 |
| 2004/0129278 A1 * | 7/2004 | Itoi | ....................... | A61F 5/3753 128/892 |
| 2006/0258966 A1 * | 11/2006 | Hargrave | .............. | A61F 5/3753 602/20 |
| 2010/0152635 A1 * | 6/2010 | Borden | .................. | A61F 5/3753 602/4 |
| 2012/0209159 A1 * | 8/2012 | Fout | ...................... | A61F 5/3753 602/4 |
| 2013/0317401 A1 * | 11/2013 | Joslin | ................... | A61F 5/3738 602/4 |

* cited by examiner

*Primary Examiner* — Tarla Patel
(74) *Attorney, Agent, or Firm* — J. Wiley Horton

(57) ABSTRACT

A modular sling and pillow system for setting an appropriate abduction angle and external rotation angle in a shoulder joint. The patient's forearm is secured in a sling. An abduction pillow is fastened to the patient's side, just above the waist and facing the elbow contained within the sling. An appropriate external rotation wedge is then attached to the abduction pillow. The external rotation wedge is preferably fastened to the abduction pillow using VELCRO fasteners so that it can be easily removed and replaced. The abduction pillow pivots the upper arm outward. The external rotation wedge rotates the upper arm by moving the wrist out away from the body. The sling is attached to the external rotation wedge so that an integral brace comprising the sling, the external rotation wedge, and the abduction pillow is created.

18 Claims, 10 Drawing Sheets

MODULAR SHOULDER EXTERNAL ROTATION WEDGE SYSTEM AND METHOD

CROSS-REFERENCES TO RELATED APPLICATIONS

This application is a non-provisional application claiming priority to U.S. Provisional Application No. 61/642,666 filed on May 4, 2012.

STATEMENT REGARDING FEDERALLY SPONSORED RESEARCH OR DEVELOPMENT

Not Applicable.

MICROFICHE APPENDIX

Not Applicable

BACKGROUND OF THE INVENTION

1. Field of the Invention

This invention relates to the field of medical products. More specifically, the invention comprises a modular arm sling system which can be used to adjust the amount of external rotation of the shoulder joint—particularly following shoulder surgery.

2. Description of the Related Art

Shoulder surgeries are now most often performed using minimally invasive techniques. Even so, the shoulder joint must be immobilized for a period after the surgery in order to promote proper healing. The proper positioning of the shoulder joint during the post-surgical period promotes a successful outcome. However, it is not necessarily desirable to use a single position during the entire healing process.

The ultimate range of motion obtained by the patient is now known—in some instances—to be dependent on the amount of external rotation of the shoulder joint that is established during the healing process. It is desirable to increase the amount of external rotation available over time. The present invention seeks to achieve this objective.

FIG. 1 shows a patient positioned to receive an immobilizing sling. Patient 10 has upper arm 12 positioned proximate lateral chest 18. Forearm 14 is positioned in front of the abdomen, just above waist 16.

FIG. 2 shows the same patient after sling 20 has been placed around her arm. Slings similar to the one shown in FIG. 2 are well known in the art. However, the specific sling illustrated (which forms a part of the present inventive system) is unique and is therefore not designated "prior art."

The sling is preferably made of a breathable fabric which has a VELCRO loop covering on its exterior. Shoulder strap 22 is connected to a posterior portion of the sling. It passes over the shoulder and connects to sling 20 near the patient's hand. Clip 24 is provided with a VELCRO hook covering so that when it is pressed against the loop covering on the exterior of sling 20 it stays in place. Thus, the user may attach shoulder strap 22 to sling 20 in a suitable position according to the particular patient's anatomy.

Release 26 is preferably a snap-type quick release. This allows the patient or practitioner to easily detach and reattach the shoulder strap without shifting the anchor point set by clip 24. Pad 38 is preferably provided to spread the load of the shoulder strap more evenly across the patient's shoulder.

For many procedures, it is desirable to abduct the shoulder joint to some extent prior to immobilizing it. Returning to FIG. 1, abducting the shoulder joint generally refers to pivoting upper arm 12 away from lateral chest 18. FIG. 3 shows a device which is commonly used for this purpose. Abduction pillow 34 is attached to the patient by circling belt 28 around the patient's waist. Male release 32 is then snapped into female release 30.

An innovative feature of the version shown is the inclusion of hook panel 36 (a strip of VELCRO hook material) on the outward facing surface of the abduction pillow. Once the patient's arm is properly positioned, the user pressed the sling against the abduction pillow. Hook panel 36 then engages the VELCRO loop covering on the outward facing surfaces of the sling and holds the sling and abduction pillow in the desired position.

FIG. 4 shows the installed abduction pillow 34 and sling 20. The position shown is considered to be a "neutral" position. The shoulder joint is abducted somewhat (pivoted outward) but is not rotated internally or externally. FIG. 5 shows the same assembly from a raised position looking downward. Neutral axis 40 is shown extending outward along the approximate centerline of the patient's forearm. Abduction pillow 35 and sling 20 maintain the forearm on this neutral axis. However, in many instances it will be desirable to adjust the external rotation of the shoulder joint off the neutral axis. The present invention provides this capability.

BRIEF SUMMARY OF THE PRESENT INVENTION

The present invention comprises a modular sling and pillow system for setting an appropriate abduction angle and external rotation angle in a shoulder joint. The patient's forearm is secured in a sling. An abduction pillow is fastened to the patient's side, just above the waist and facing the elbow contained within the sling. An appropriate external rotation wedge is then attached to the abduction pillow. The external rotation wedge is preferably fastened to the abduction pillow using VELCRO fasteners so that it can be easily removed and replaced.

The abduction pillow pivots the upper arm outward. The external rotation wedge rotates the upper arm by moving the wrist out away from the body. The side of the external rotation wedge preferably includes one or more VELCRO fasteners which engage corresponding VELCRO material on the sling. Thus, the sling, the external rotation wedge, and the abduction pillow may all be joined together into a cohesive unit. Thus joined, the three elements maintain the shoulder joint in a desired alignment.

The external rotation wedges are preferably provided in various angles so that the user may vary the degree of external rotation established by the complete assembly. This allows a practitioner to increase the degree of external rotation employed during the post-operative period.

Figure 1:
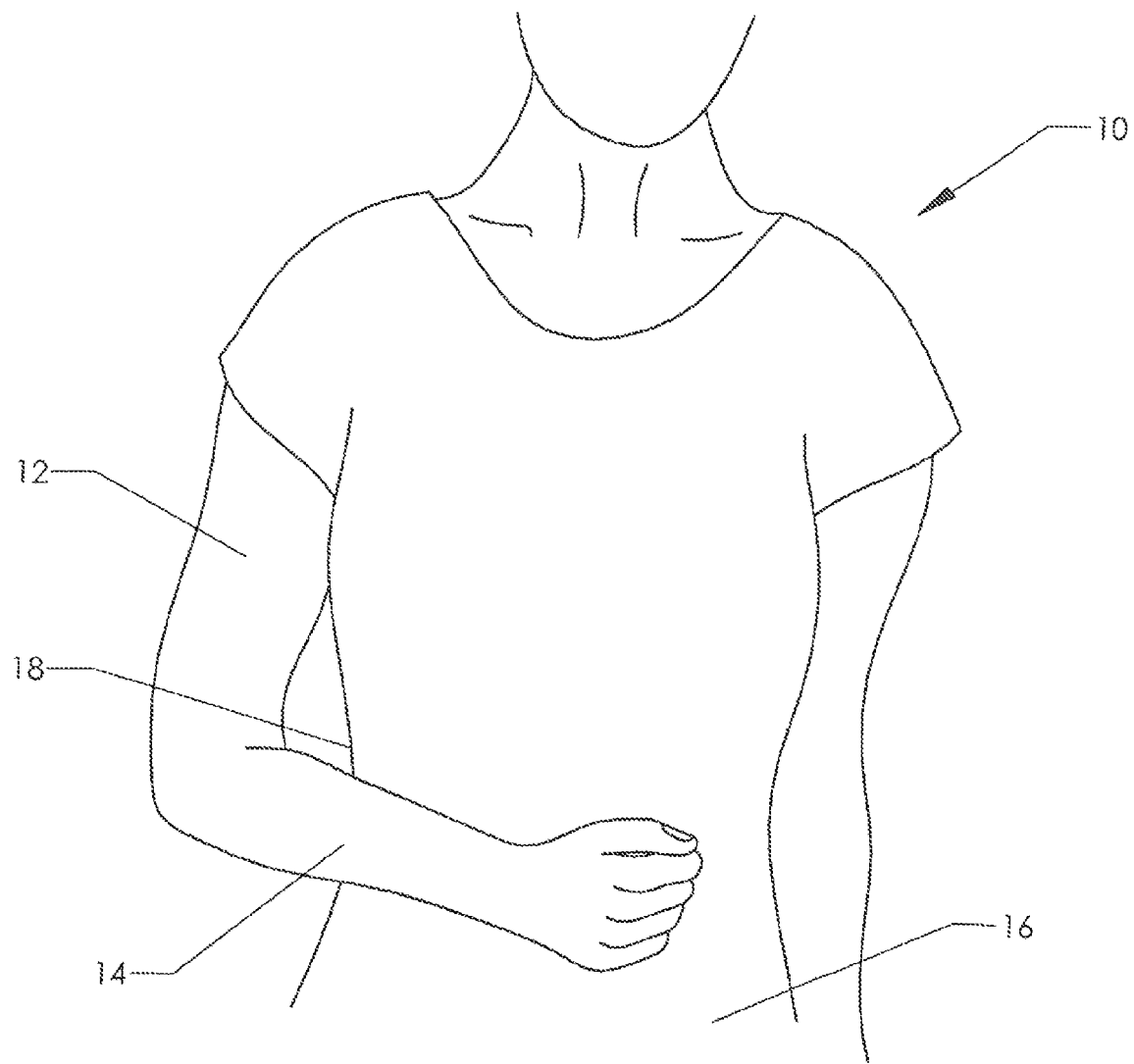
FIG. 1 is a perspective view, showing a patient with her arm positioned to receive a sling.

| REFERENCE NUMERALS IN THE DRAWINGS | |
|---|---|
| 10 patient | 12 upper arm |
| 14 forearm | 16 waist |
| 18 lateral chest | 20 sling |
| 22 shoulder strap | 24 clip |
| 26 release assembly | 28 belt |
| 30 female release | 32 male release |
| 34 abduction pillow | 36 hook panel |
| 38 pad | 40 neutral axis |
| 42 external rotation wedge (15°) | 44 external rotation wedge (30°) |
| 46 hook panel | 48 hook panel |
| 50 hook panel | 52 hook panel |
| 54 wedge portion | 56 front portion |
| 58 corner | 60 anterior surface |
| 62 body relief | 64 external rotation axis |
| 66 lateral surface | 68 lateral surface |
| 70 lateral mounting surface | 72 posterior mounting surface |
| 74 corner | |

DETAILED DESCRIPTION OF THE INVENTION

Figure 5:
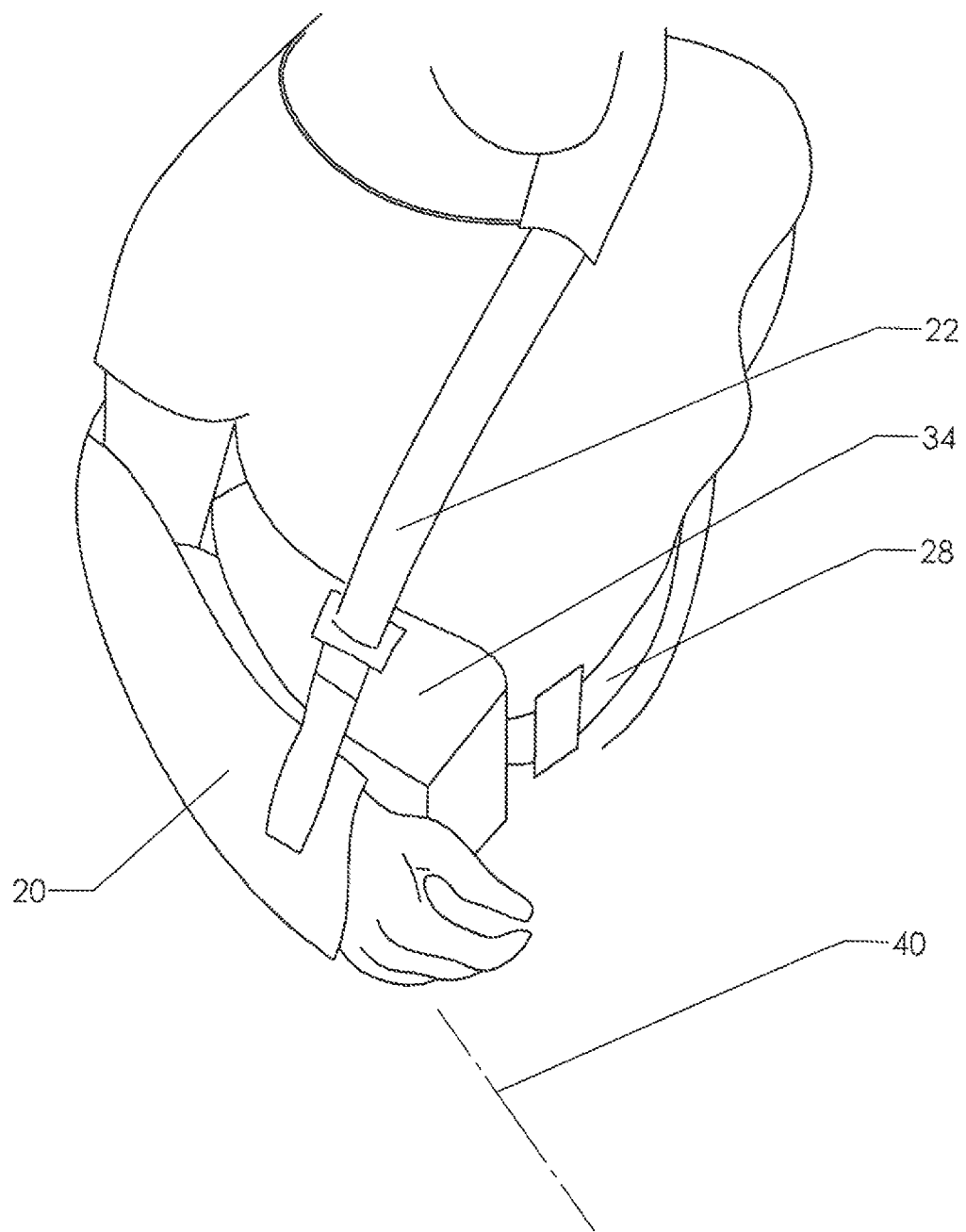
FIG. 5 is a perspective view, showing the same configuration as FIG. 4 from an elevated perspective looking downward.

FIG. 5 shows the patient's shoulder joint in a stabilized position. Sling 20 is attached to abduction pillow 34, which is attached to the patient via belt 28. Shoulder strap 22 supports the forward portion of the sling, proximate the patient's wrist.

As explained previously, the present invention preferably provides a number of features which make the creation of the assembly shown in FIG. 5 more convenient. The use of hook-and-loop (VELCRO) fasteners to join the sling to the abduction pillow allows the sling to be properly positioned despite a wide variation in patient anatomy. The use of the release assemblies on belt 28 and shoulder strap 22 also allows the device to be easily installed and removed without altering its adjusted position.

FIG. 5 shows an orientation in which the user's forearm is roughly aligned with neutral axis 40. The shoulder joint is abducted somewhat—meaning that the upper arm is pivoted outward with respect to the lateral chest wall. However, no external rotation has been applied. The term "external rotation" is defined with respect to the upper arm, the forearm, and the elbow. External rotation is created by keeping the upper arm and elbow in the same position while moving the wrist outward away from the body. This motion externally rotates the shoulder joint.

FIG. 5 shows the patient's wrist in the neutral position (lying on neutral axis 40). If the wrist is moved toward the waist then internal rotation is produced. If the wrist is moved outward then external rotation is produced.

It has been discovered that some degree of external rotation established during the "fixation" period is beneficial to the patient's ultimate recovery from shoulder surgery. The degree of desired external rotation varies. It may also be helpful in some instances to gradually increase the degree of external rotation during the healing process. Thus, simply reshaping the abduction pillow to provide more external rotation is not an optimal solution.

Figure 6:
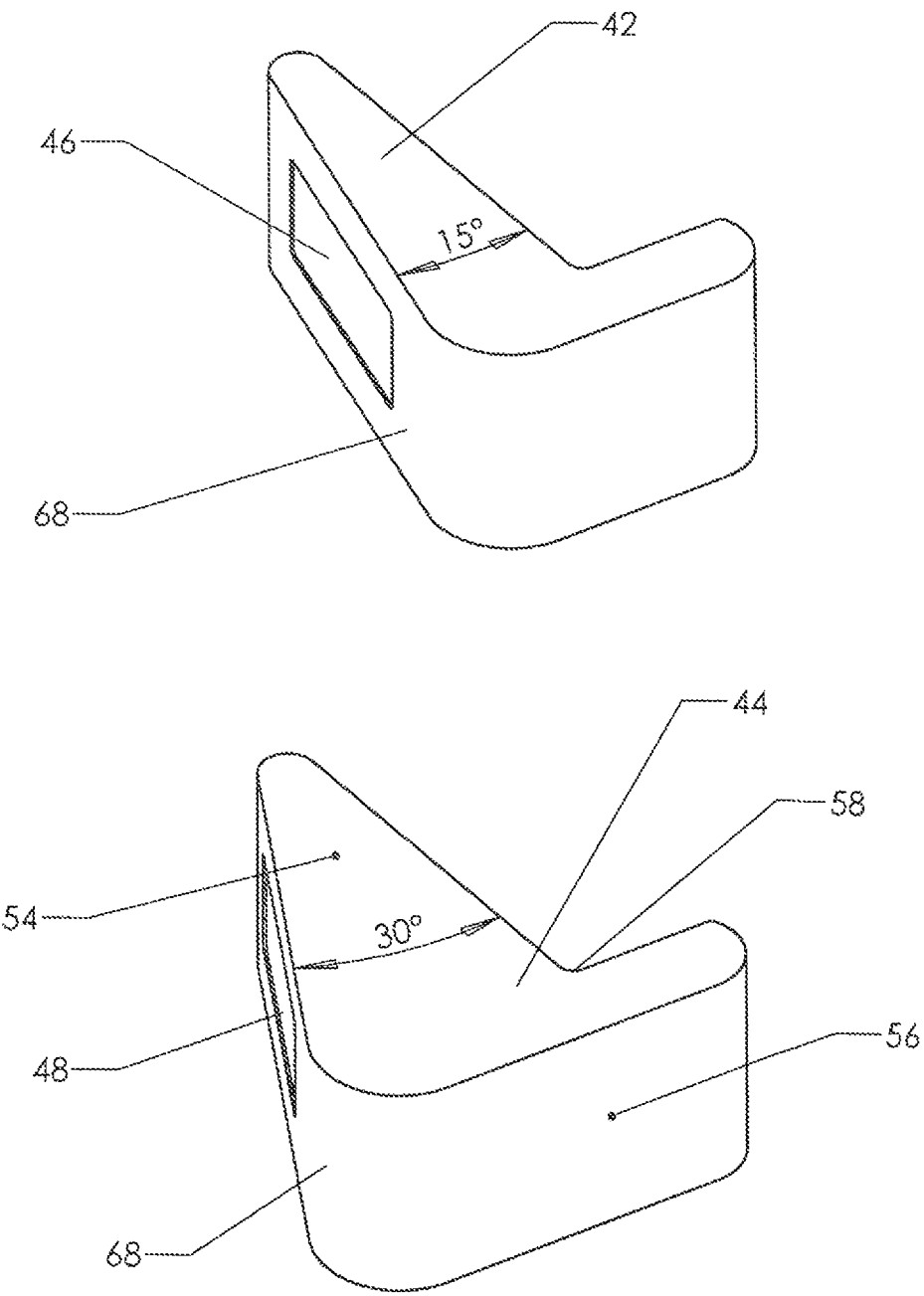
FIG. 6 is a perspective view showing two external rotation wedges.
Figure 7:
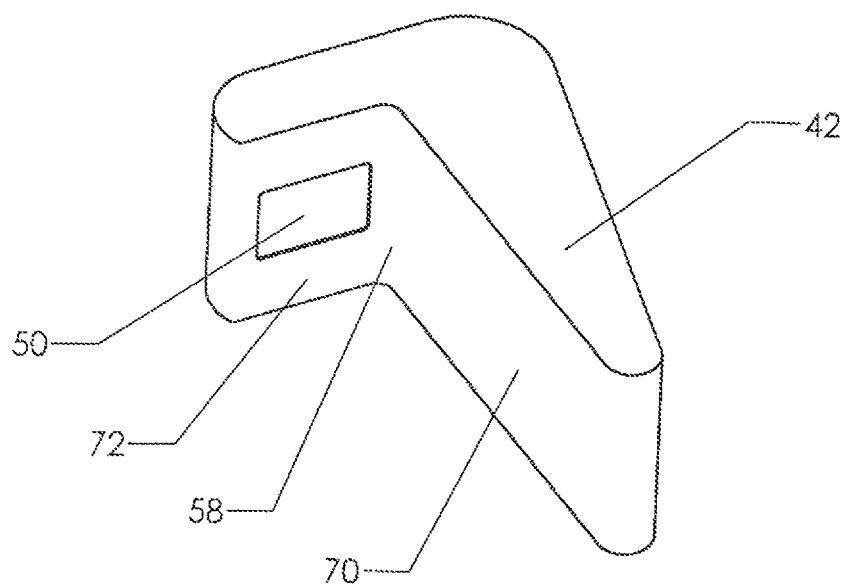
FIG. 7 is a perspective view showing the external rotation wedges of FIG. 6 from a different vantage point.
Figure 7:
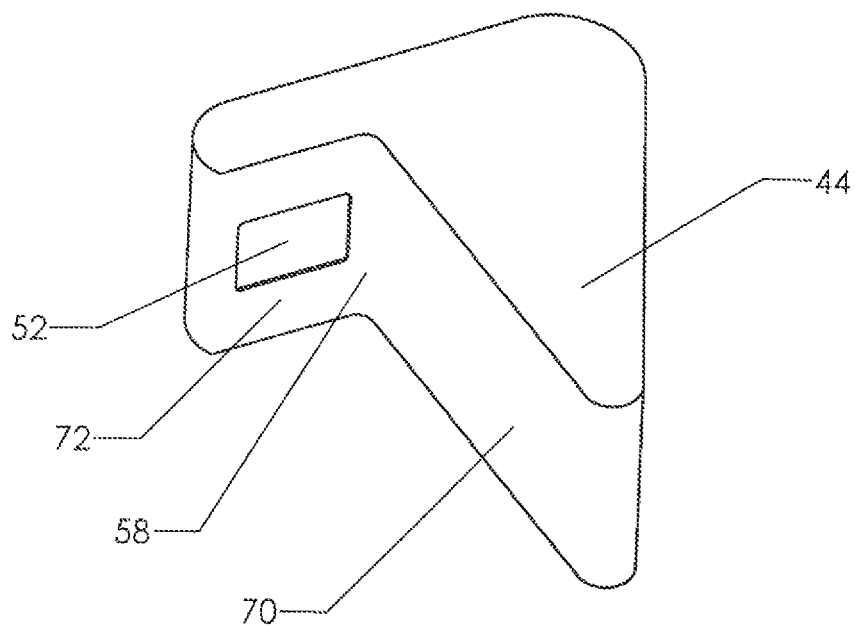

The present invention takes a different approach. FIGS. 6 and 7 depict a pair of external rotation wedges. These wedges are designed to be added to the abduction pillow. It is preferable to provide a plurality of external rotation wedges with differing amounts of angular offset. External rotation wedge 42 provides 15 degrees of external rotation whereas external rotation wedge 44 provides 30 degrees of external rotation.

Each external rotation wedge includes a lateral surface 68. This lateral surface includes a hook panel (hook panel 46 for the upper rotation wedge and hook panel 48 for the lower one). Wedge portion 54 includes a fixed angular displacement. Front portion 56 faces forward. The wedge is roughly in an "L" shape when viewed from above—with the two portions joining at corner 58.

FIG. 7 shows the same pair of external rotation wedges from the opposite side. Posterior mounting surface 72 is intended to face toward the rear, while lateral mounting surface 70 is intended to face toward the side of the patient. Each posterior mounting surface 72 includes a hook panel (hook panel 50 on the upper wedge and hook panel 52 on the lower wedge). Corner 58 is formed by the intersection of the posterior mounting surface and the lateral mounting surface. The lateral mounting surface is preferably covered with loop material.

The angle between lateral mounting surface 70 and lateral surface 68 (shown in FIG. 6) defines the degree of external rotation provided by the particular wedge. The angular displacement between these surfaces is 15 degrees for the wedge shown at the top of the view. The angular displacement is 30 degrees for the wedge shown at the bottom of the view. A variety of angular displacements are preferably provided so that a physician or physical therapist is able to select the right amount for each particular patient.

Figure 8:
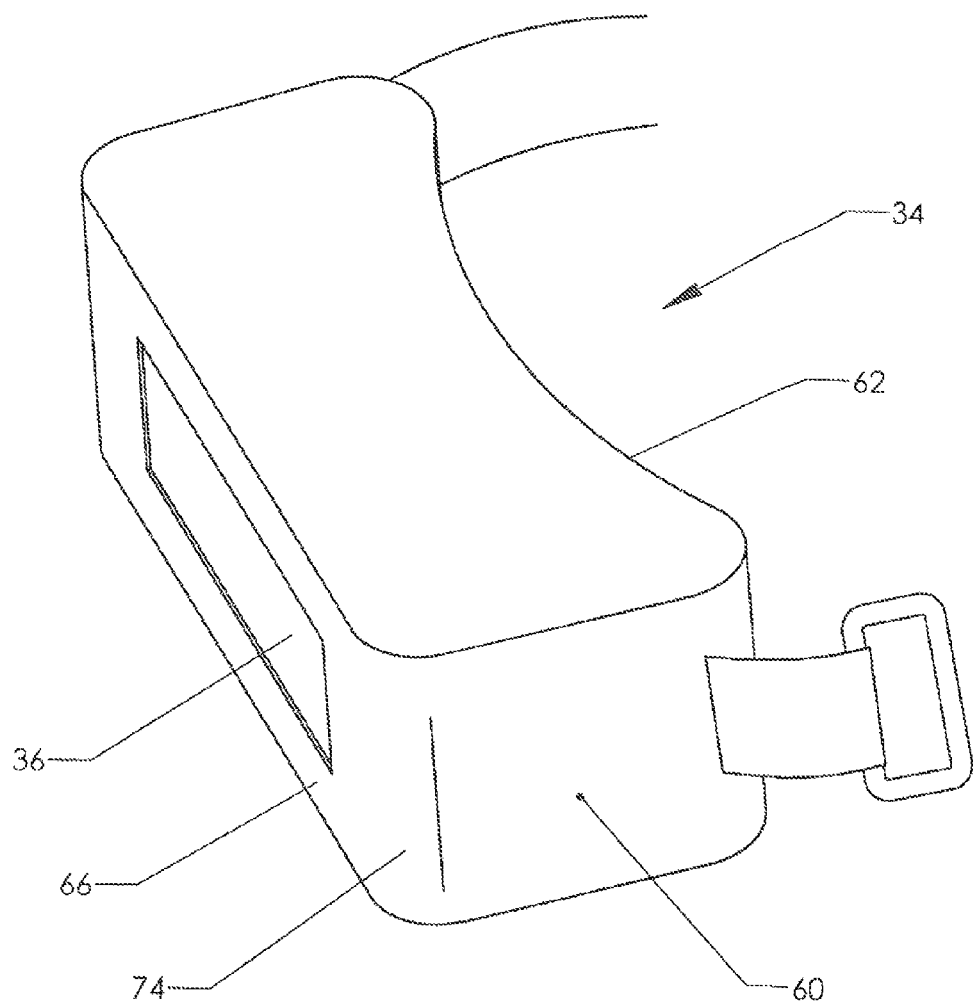
FIG. 8 is a perspective view, showing the abduction pillow of FIGS. 4 and 5 in more detail.

FIG. 8 shows a detailed perspective view of abduction pillow 34. Body relief 62 is provided to conform the pillow to the user's side. The inward facing surface (not shown) is preferably provided with a material which holds the pillow in position. Anterior surface 60 is preferably covered in loop material. Lateral surface 66 includes a hook panel 36. Corner 74 is formed by the intersection of anterior surface 60 and lateral surface 66.

Returning now to FIG. 7, an external rotation wedge is designed to attach to the abduction pillow by mating corner 58 on the wedge with corner 74 on the abduction pillow. The external rotation wedges are preferably made of pliable material (such as a fabric covered foam) so that the user can bend the two legs of the "L" outward. The user then presses corner 58 against corner 74 and presses the two legs back inward. The loop covering on lateral mounting surface 70 engages hook panel 36 on abduction pillow 34. Likewise, hook panel 52 on the abduction wedge engages the loop covering on anterior surface 60 on the abduction pillow.

Figure 9:
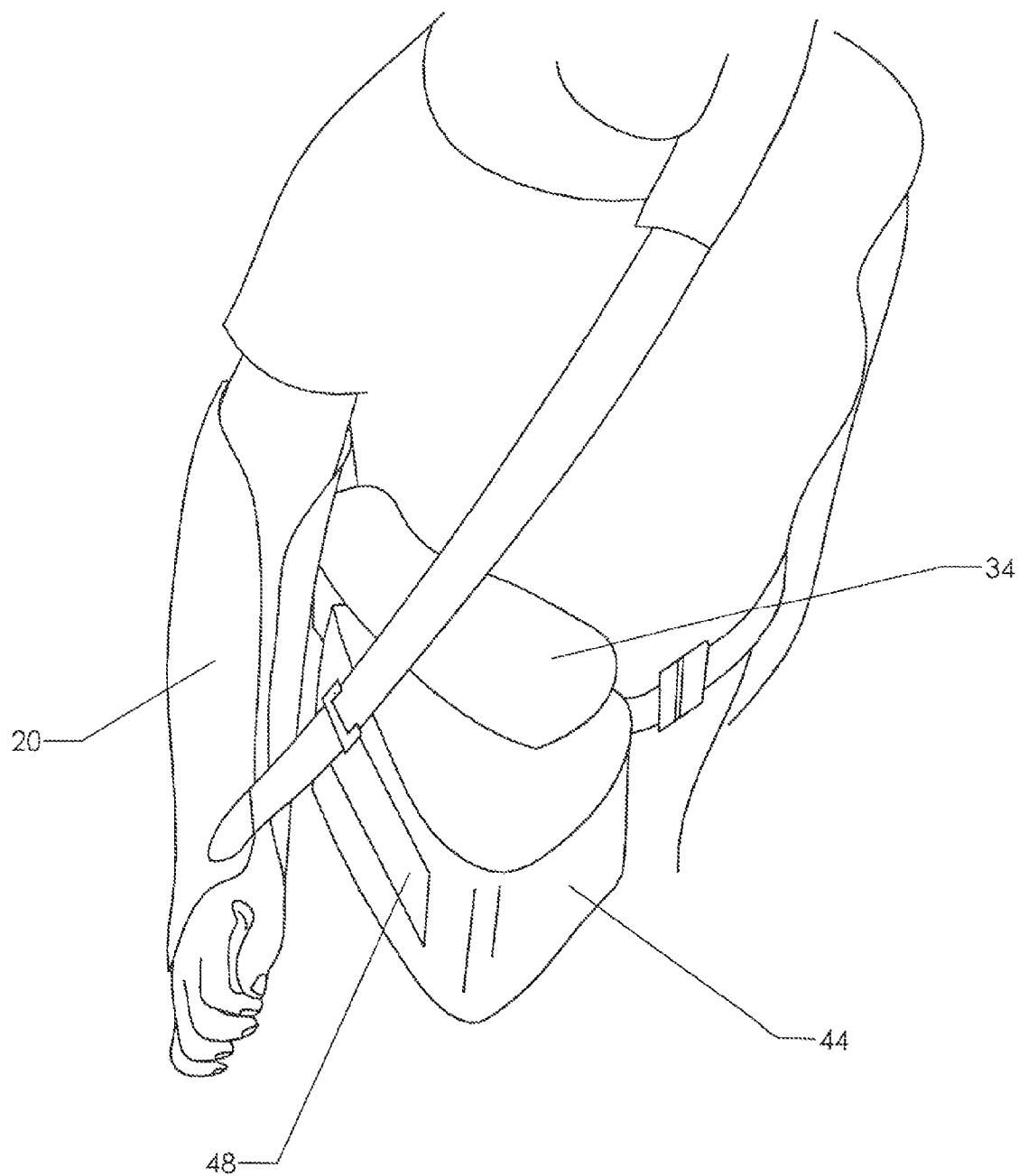
FIG. 9 is a perspective view, showing the installation of an external rotation wedge on an abduction pillow.

FIG. 9 shows external rotation wedge 44 (having 30 degrees of angular displacement) installed on abduction pillow 34. The reader will observe how hook panel 48 faces outward toward sling 20. The sling is covered in loop material so that when the sling is pressed inward against hook panel 48 it will become attached to the external rotation wedge.

Figure 10:
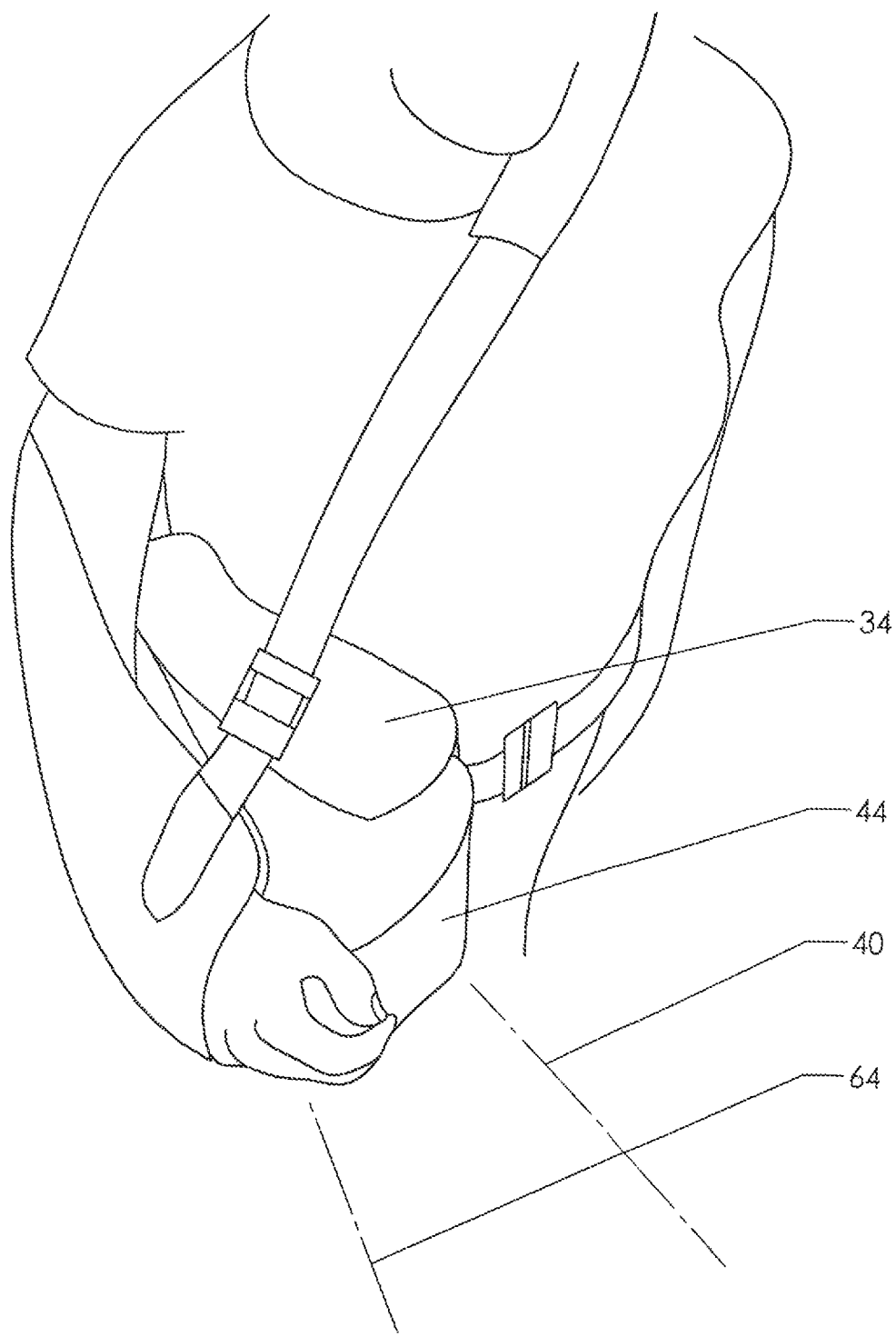
FIG. 10 is a perspective view, showing the complete assembly of the abduction pillow, the external rotation wedge, and the sling.

FIG. 10 shows the patient after the sling has been attached to the abduction pillow. The external rotation wedge has rotated the forearm outward so that the centerline of the forearm (external rotation axis 64) is rotated well away from neutral axis 40.

The external rotation wedge can be attached to the abduction pillow using a wide variety of fasteners. However, hook-and-loop fasteners are preferred for convenience. Looking back at FIG. 9, the reader will appreciate that a user simply "peels" the sling away from its attachment to the external rotation wedge (or the abduction pillow itself if no wedge is present) to place the arm in the position shown in FIG. 9. The user may then add or exchange an external rotation wedge and place the sling back in contact.

As one example, the user could start with a wedge having a relatively small angular displacement (such as 5 degrees) for the week after surgery. This could then be exchanged for an external rotation wedge having a 15 degree angular displacement in the next week. A wedge having even greater angular displacement could be added subsequently.

The invention's components have numerous features allowing for the convenient changing of the external rotation wedge. VELCRO-type hook-and-loop fasteners are preferred, since these allow the components to be easily assembled, disassembled, and repositioned. The use of release assemblies on the shoulder straps and the belt for the abduction assembly also facilitate removal and reinstallation.

Figure 2:
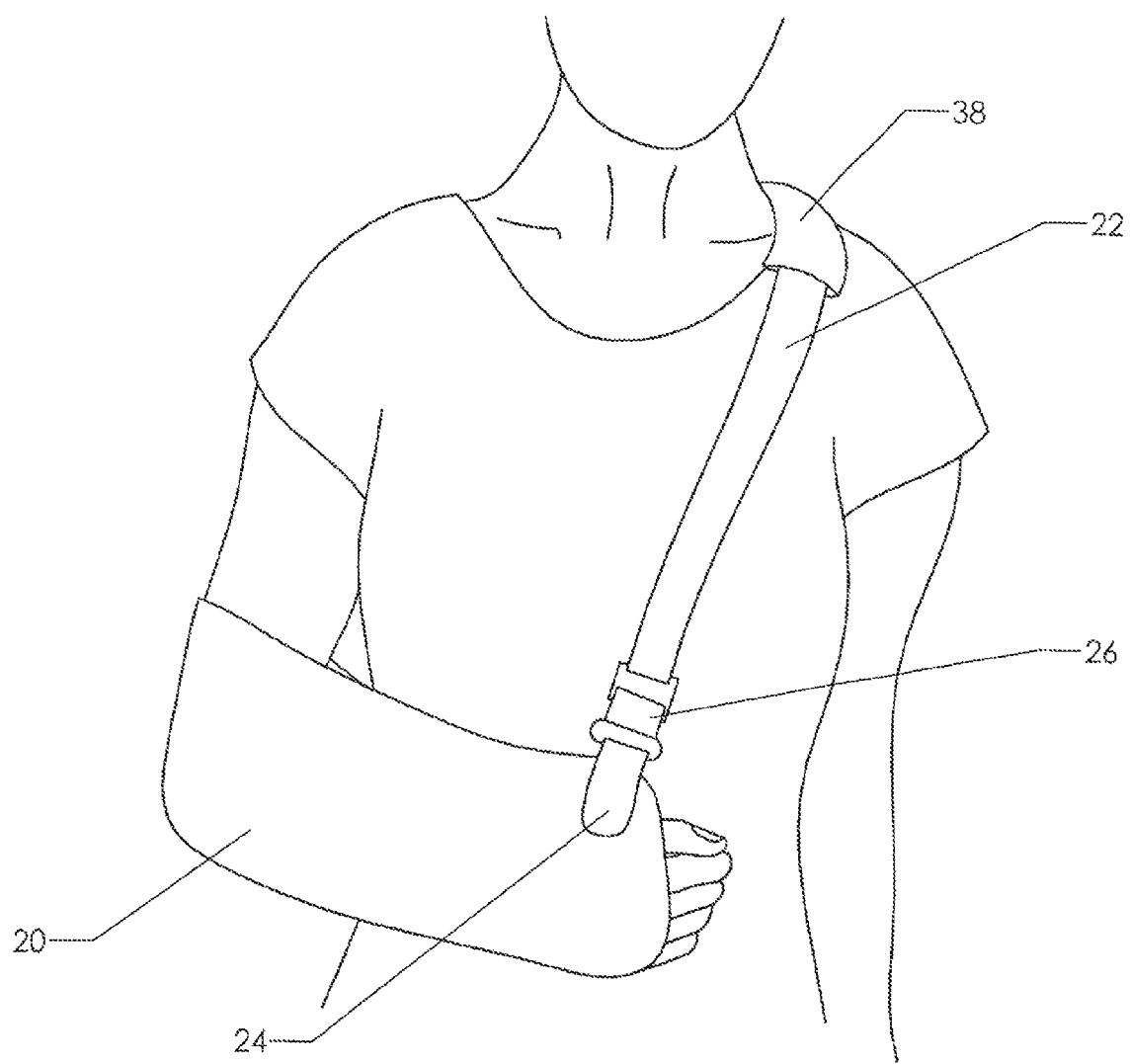
FIG. 2 is a perspective view, showing the patient of FIG. 1 with a sling installed.
Figure 3:
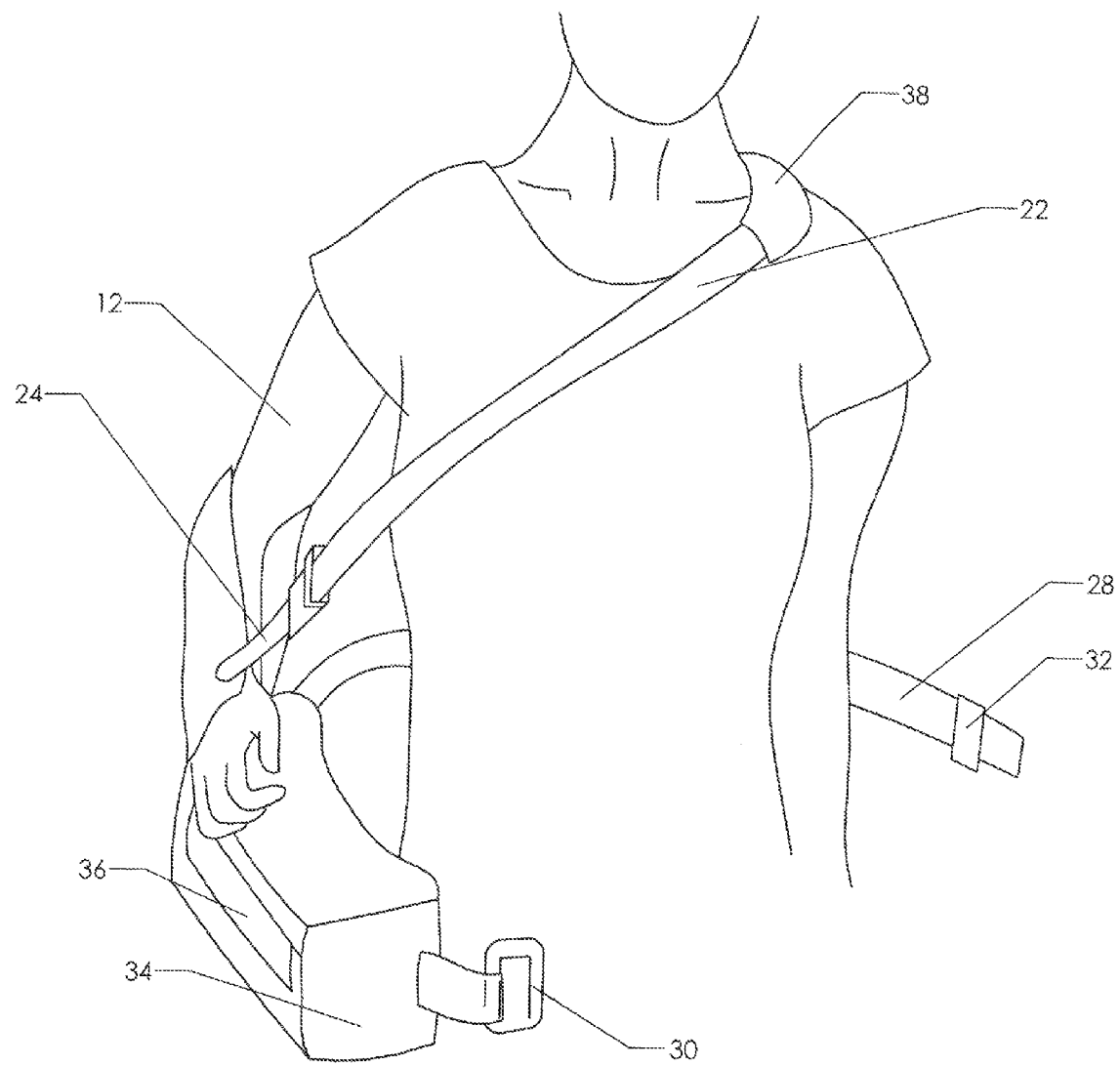
FIG. 3 is a perspective view, showing the installation of an abduction pillow.
Figure 4:
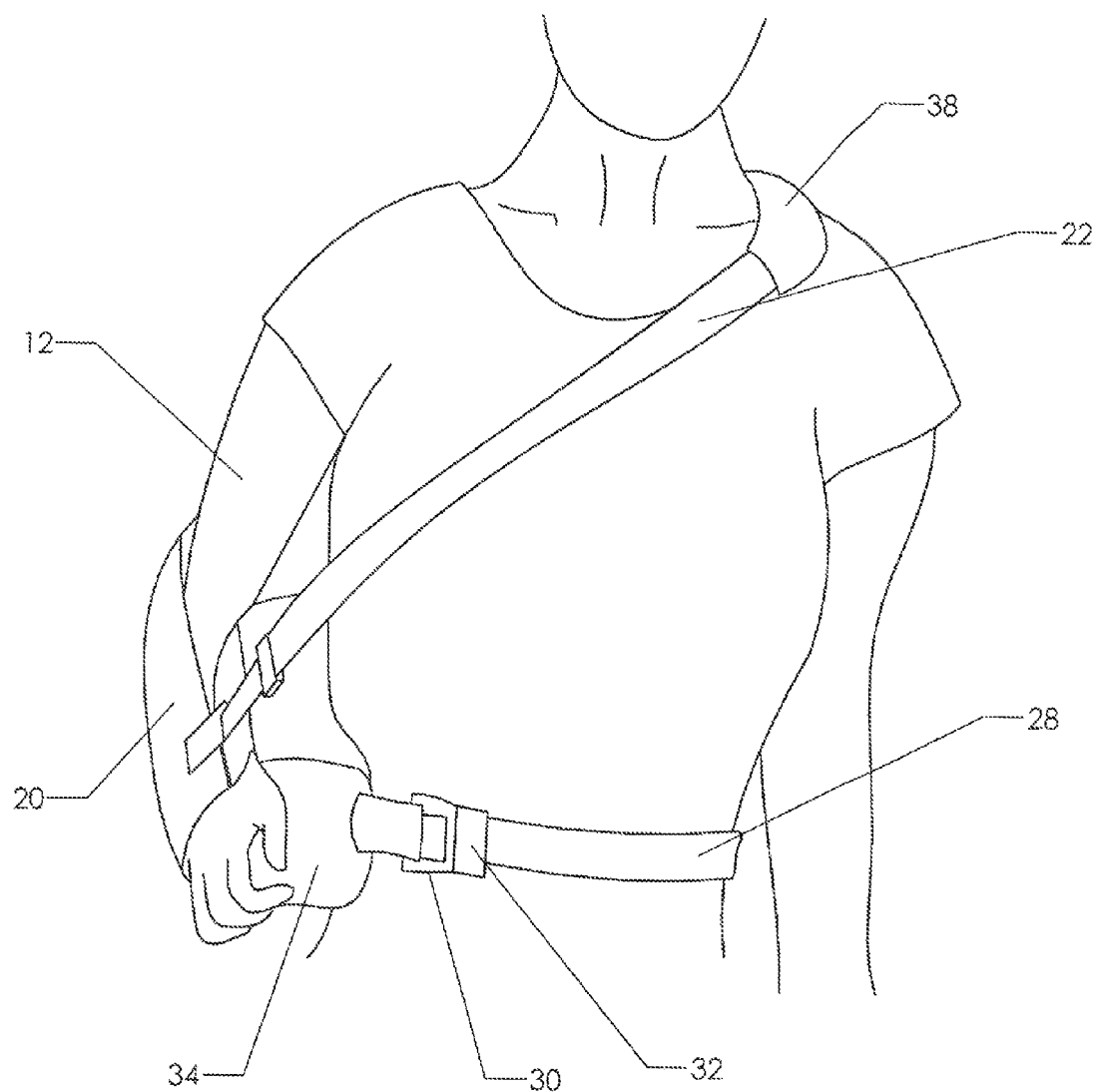
FIG. 4 is a perspective view, showing the abduction pillow in an installed position.

As the forearm is rotated externally it may ultimately be desirable to reposition the anchor point for the shoulder strap on the sling. FIG. 2 shows shoulder strap 22 being attached to sling 20 by clip 24. The clip is a "butterfly" arrangement of two inward facing hook patches. The reader will recall that the exterior of sling 20 is preferably covered in loop material. FIG. 3 shows how the "butterfly" of clip 24 can be split over the top of the sling material so that the hook panel facing outward is pressed against the inward facing part of the sling and the hook panel facing inward is pressed against the outward facing part of the sling.

The user may thereby position clip 24 anywhere along the upper part of the sling. Thus, when the amount of external rotation is varied, the user can easily remove and reposition the clip so that shoulder strap 22 remains in a comfortable position.

Although the preceding descriptions present considerable detail they should be properly be viewed as illustrating embodiments of the present invention rather than limiting the scope of the invention. Many more embodiments following the same principles will occur to those skilled in the art. For example, snaps or buckles could be substituted for the hook-and-loop attachments described. Accordingly, the scope of the invention should be fixed by the following claims rather than by the examples given.

The invention claimed is:

1. A method for stabilizing a shoulder joint in a patient's arm in a position having a desired amount of abduction and external rotation, comprising:
   a. providing a sling;
   b. providing an abduction pillow, said abduction pillow having a lateral surface;
   c. providing an external rotation wedge, said external rotation wedge having a lateral mounting surface and said external rotation wedge having a lateral surface, with an angular displacement between said lateral mounting surface and said lateral surface;
   d. attaching said abduction pillow to said patient proximate said patient's waist proximate said arm, with said lateral surface of said abduction pillow facing outward;
   e. placing said arm in said sling;
   f. attaching said external rotation wedge to said abduction pillow with said lateral mounting surface of said external rotation wedge mating against said lateral surface of said abduction pillow;
   g. attaching said sling to said lateral surface of said external rotation wedge; providing an anterior surface on said abduction pillow;
   h. providing a posterior mounting surface on said external rotation wedge; and
   i. mating said posterior mounting surface on said external rotation wedge against said anterior surface on said abduction pillow when attaching said external rotation wedge to said abduction pillow.

2. A method for stabilizing a shoulder joint as recited in claim 1, further comprising:
   a. providing a plurality of said external rotation wedges having differing values for said angular displacement between said lateral mounting surface of said external rotation wedge and said lateral surface of said external rotation wedge; and
   b. selecting one of said external rotation wedges for installation, with said selection being made on the basis of the desired degree of external rotation of said shoulder joint.

3. A method for stabilizing a shoulder joint as recited in claim 1, further comprising:
   a. providing a hook and loop connection between said abduction pillow and said external rotation wedge; and
   b. providing a hook and loop connection between said external rotation wedge and said sling.

4. A method for stabilizing a shoulder joint as recited in claim 1, further comprising:
   a. providing a belt for attaching said abduction pillow to said patient; and
   b. providing a release assembly in said belt.

5. A method for stabilizing a shoulder joint as recited in claim 1, further comprising:
   a. providing a strap for attaching said sling to said patient; and
   b. providing a release assembly in said sling.

6. A method for stabilizing a shoulder joint as recited in claim 1, further comprising covering a substantial portion of an exterior surface of said sling in loop material.

7. A method for stabilizing a shoulder joint in a patient having an upper arm, a lateral chest proximate said upper arm, a neutral abduction position for said shoulder joint and a neutral rotation position for said shoulder joint, comprising:
   a. providing an abduction pillow, said abduction pillow having a lateral surface, a body cutout and an anterior surface, with said lateral surface being offset from said body cutout so that said abduction pillow is configured to place said shoulder joint in positive abduction so that said upper arm is pivoted outward with respect to said lateral chest wall;
   b. providing an external rotation wedge, said external rotation wedge having a lateral mounting surface, said external rotation wedge having a posterior mounting surface, and said external rotation wedge having a lateral surface, with an angular displacement between said lateral mounting surface of said external rotation wedge and said lateral surface of said external rotation wedge;

c. attaching said abduction pillow to said patient, with said lateral surface of said abduction pillow facing outward toward said arm and said anterior surface facing forward;
d. attaching said external rotation wedge to said abduction pillow with said lateral mounting surface of said external rotation wedge facing said lateral surface of said abduction pillow and said posterior mounting surface of said external rotation wedge facing said anterior surface of said abduction pillow;
e. providing a sling;
f. placing said arm in said sling; and
g. attaching said sling to said lateral surface of said external rotation wedge.

8. A method for stabilizing a shoulder joint as recited in claim 7, further comprising:
    a. providing a plurality of said external rotation wedges having differing values for said angular displacement between said lateral mounting surface of said external rotation wedge and said lateral surface of said external rotation wedge; and
    b. selecting one of said external rotation wedges for installation, with said selection being made on the basis of the desired degree of external rotation of said shoulder joint.

9. A method for stabilizing a shoulder joint as recited in claim 8, further comprising:
    a. providing a hook and loop connection between said abduction pillow and said external rotation wedge; and
    b. providing a hook and loop connection between said external rotation wedge and said sling.

10. A method for stabilizing a shoulder joint as recited in claim 7, further comprising:
    a. providing a hook and loop connection between said abduction pillow and said external rotation wedge; and
    b. providing a hook and loop connection between said external rotation wedge and said sling.

11. A method for stabilizing a shoulder joint as recited in claim 7, further comprising:
    a. providing a belt for attaching said abduction pillow to said patient; and
    b. providing a release assembly in said belt.

12. A method for stabilizing a shoulder joint as recited in claim 7, further comprising:
    a. providing a strap for attaching said sling to said patient; and
    b. providing a release assembly in said sling.

13. A method for stabilizing a shoulder joint as recited in claim 7, further comprising covering a substantial portion of an exterior surface of said sling in loop material.

14. A method for stabilizing a shoulder joint in a patient's arm, comprising:
    a. providing an abduction pillow, said abduction pillow having a lateral surface;
    b. providing an external rotation wedge, said external rotation wedge having a lateral mounting surface and said external rotation wedge having a lateral surface, with an angular displacement between said lateral mounting surface of said external rotation wedge and said lateral surface of said external rotation wedge;
    c. attaching said abduction pillow to said patient, with said lateral surface of said abduction pillow facing outward toward said arm;
    d. attaching said external rotation wedge to said abduction pillow with said lateral mounting surface of said external rotation wedge facing said lateral surface of said abduction pillow;
    e. providing a sling;
    f. placing said arm in said sling;
    g. attaching said sling to said lateral surface of said external rotation wedge;
    h. providing an anterior surface on said abduction pillow;
    i. providing a posterior mounting surface on said external rotation wedge; and
    j. mating said posterior mounting surface on said external rotation wedge against said anterior surface on said abduction pillow when attaching said external rotation wedge to said abduction pillow.

15. A method for stabilizing a shoulder joint as recited in claim 14, further comprising:
    a. providing a plurality of said external rotation wedges having differing values for said angular displacement between said lateral mounting surface of said external rotation wedge and said lateral surface of said external rotation wedge; and
    b. selecting one of said external rotation wedges for installation, with said selection being made on the basis of the desired degree of external rotation of said shoulder joint.

16. A method for stabilizing a shoulder joint as recited in claim 14, further comprising:
    a. providing a hook and loop connection between said abduction pillow and said external rotation wedge; and
    b. providing a hook and loop connection between said external rotation wedge and said sling.

17. A method for stabilizing a shoulder joint as recited in claim 14, further comprising:
    a. providing a belt for attaching said abduction pillow to said patient; and
    b. providing a release assembly in said belt.

18. A method for stabilizing a shoulder joint as recited in claim 14, further comprising:
    a. providing a strap for attaching said sling to said patient; and
    b. providing a release assembly in said sling.

* * * * *